(12) United States Patent
Kagan et al.

(10) Patent No.: US 6,258,979 B1
(45) Date of Patent: Jul. 10, 2001

(54) CHIRAL FERROCENE PHOSPHINES ACTIVE IN ASYMMETRIC CATALYSIS

(76) Inventors: Henri Kagan, 10 rue Georges Clemenceau, 91400 Orsay (FR); Gilles Argouarch, 1 Square Cormier, Rennes (FR), 35200; Odile Samuel, 160 Residence Eaux Vives, Palaiseau (FR), 91120

( * ) Notice: Subject to any disclaimer, the term of this patent is extended or adjusted under 35 U.S.C. 154(b) by 0 days.

(21) Appl. No.: 09/444,858

(22) Filed: Nov. 22, 1999

(51) Int. Cl.7 .................................................... C07C 229/00
(52) U.S. Cl. .......................... 562/450; 562/496; 562/590; 564/301; 564/336
(58) Field of Search ..................... 562/512, 443, 562/496, 480, 450, 590; 556/13, 19, 21, 22; 564/301, 336, 300; 502/162, 166

(56) References Cited

U.S. PATENT DOCUMENTS 5,563,309 * 10/1996 Togni et al. ........................ 585/277

FOREIGN PATENT DOCUMENTS

2289855 * 12/1995 (GB) .

* cited by examiner

*Primary Examiner*—Jean F. Vollano
(74) *Attorney, Agent, or Firm*—Schnader Harrison Segal & Lewis LLP

(57) ABSTRACT

The invention pertains to chiral ferrocene phosphine derivatives and their use with transition metals as asymmetric catalysts in asymmetric hydrogenation.

7 Claims, No Drawings

CHIRAL FERROCENE PHOSPHINES ACTIVE IN ASYMMETRIC CATALYSIS

The present invention pertains to new compounds of formula (I), chiral ferrocene phosphine derivatives, and their use in asymmetric catalysis, more specifically in asymmetric hydrogenation.

The compounds of formula (I) are defined as below:

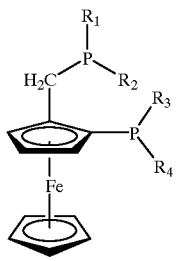

(I)

in which R1, R2, R3, and R4 are identical or different and represent a group selected from among hydrogen, a linear or branched $C_{1-7}$ alkyl, a $C_{5-7}$ cycloalkyl possibly substituted by a $C_{1-4}$ alkyl, a trifluoromethyl, a halogen, a hydroxy or an alkoxy, a phenyl possibly substituted by a $C_{1-4}$ alkyl, a trifluoromethyl, a halogen, a hydroxy or an alkoxy.

The invention also covers all of the optically active forms of the compounds of formula (I).

The synthesis of optically active functionalized compounds such as, for example, the amino acids, the mono- or dicarboxylic acids, presently represents an important industrial activity. There is therefore a requirement for catalytic systems for the synthesis of these alcohols and amines which are increasingly competitive in terms of both cost and efficacy.

Known from the European patents "EP 612758" and "EP 646590", published by Ciba-Geigy, are catalytic systems combining a rhodium or iridium complex of the type [Ir(1, 5-cyclooctadiene)Cl]$_2$, [Rh(norbornadiene)$_2$Cl]$_2$ or [Rh(norbornadiene)$_2$]BF$_4$ with an enantiomerically pure organic ligand such as the ferrocene phosphines, such as, for example, the ligand "JOSIPHOS".

These catalytic systems enable the transformation of certain functionalized enamides, ketones or alkenes such as, for example, acetamidocinnamic acid (or the alkyl ester), itaconic acid (or the alkyl ester), acetyl acetic acid (or the alkyl ester) into corresponding chiral compounds.

The object of the present invention is the introduction of new ligands of the ferrocene phosphine type of formula (I), characterized by high performance in terms of activity and enantioselectivity for the synthesis of chiral compounds.

For this purpose, the ligands of formula (I) according to the invention are prepared from the compound of formula (II) according to the procedure described in the article J. Org. Chem. 1997, 62, p. 6733, by the authors O. Riant, O. Samuel, T. Flessner, S. Taudien and H. B. Kagan.

The compounds of formula (II) are defined as below:

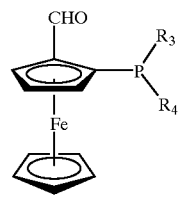

(II)

in which R3 and R4 have the same meanings as in formula (I).

The compound of formula (II) is reduced by a hydride so as to obtain compound (III) as defined below:

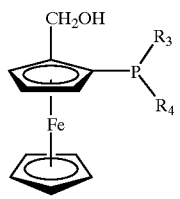

(III)

in which R3 and R4 have the same meanings as in formula (I).

The compound of formula (III) then has its hydroxyl group substituted so as to produce the compounds of formula (I).

The invention also has as its object the use of derivatives of formula (I) as ligands in an enantioselective reduction process for unsaturated compounds of formula (IV). Said unsaturated compounds are more specifically enamides or compounds with a carbon-carbon double bond.

The compounds of formula (IV) are represented below:

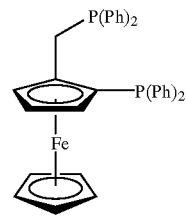

in which R5 and R6 are different, with R5 selected from among a $C_{1-5}$ alkyl; an aryl group; an aryl group substituted by a $C_{1-4}$ alkyl, a $C_{1-4}$ alkoxy or a halogen; a heteroaryl group substituted by a $C_{1-4}$ alkyl, a $C_{1-4}$ alkoxy or a halogen; a carboxylic acid; a carboxylic ester; a $C_{1-4}$ alkyl carboxylic acid; a $C_{1-4}$ alkyl carboxylate; with R6 selected from among an amide; an aryl; an aryl substituted by a $C_{1-4}$ alkyl, a $C_{1-4}$ alkoxy or a halogen heteroaryl; a heteroaryl substituted by a $C_{1-4}$ alkyl, a $C_{1-4}$ alkoxy or a halogen; in which Z is represented by an NR7, NOR7 or C(R7)$_2$ group, with R7 selected from among hydrogen; a $C_{1-5}$ alkyl; an aryl group possibly substituted by a $C_{1-4}$ alkyl; a halogen or an alkoxyalkyl; a heteroaryl group possibly substituted by a $C_{1-4}$ alkyl or a halogen or an alkoxyalkyl.

In the implementation of the catalytic system, the transition metal is preferably rhodium and the complexes are of the type [Rh(formula (I))(COD)]BF$_4$ or [Rh(formula (I))COD]PF$_6$ or [Rh(formula (I))(C1)COD].

The reaction is perferably carried out in a temperature range of 20–100° C.

The catalytic quantity of the rhodium complex in relation to the quantity of formula (IV) substrate is from 1 to 50,000, preferably from 100 to 20,000, and especially preferably from 1000 to 10,000.

As the examples to be presented below will show, these new formula (I) ligands exhibit high performance in terms of catalytic activity.

Experimental Part

Preparation of the Ligand

EXAMPLE 1

($S_{Fc}$)-1-dicyclohexylphosphinomethyl-2-diphenylphosphinoferrocene

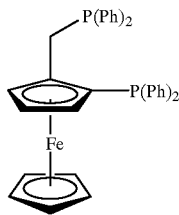

EXAMPLE 1A ($S_{Fc}$)-1-hydroxymethyl-2-diphenylphosphinoferrocene

Into a flask equipped with a reflux condenser, one places under argon 6.37 g of ($S_{Fc}$)-2-diphenylphosphinoferrocene carboxaldehyde (M=398.24; 16 mmol) and 0.38 g of sodium borohydride (M=37.83; 10 mmol) in solution in 150 ml of degassed absolute ethanol and one heats for 4 hours at 45° C.; the color passes from red to orange. After returning to ambient temperature, the ethanol is evaporated and the product is taken up with ether. Hydrolysis is performed by addition of 50 ml of water, followed by extraction with ether and washing with water. After drying over MgSO$_4$, filtration and elimination of the solvents, one obtains 6.4 g of an orange product.

Over this crude product, one adds 120 ml of hexane and 60 ml of ether. The mixture is brought to reflux until obtaining a clear solution and then slowly brought to ambient temperature and placed at −24° C. The crystals formed are filtered and rinsed with 100 ml of hexane. After this first recrystallization, one recovers 5.14 g of product. The mother liquors are concentrated and then purified by flash chromatography on a small height of silica gel. By eluting with a hexane/ethyl acetate mixture (3:1), one isolates a majority fraction (0.86 g). A second recrystallization is performed on this fraction with 10 ml of hexane and 3 ml of ether which enables isolation of 0.76 g of orange crystals. One obtains a total mass of recrystallized product of 5.9 g (14.7 mmol) which corresponds to a yield of 92%.

mp=102–103° C.

$[\alpha]_D$=−282 (c=1.00; CHCl$_3$)

$^1$H NMR (250 MHz, CDCl$_3$): δ7.51–7.46 (m, 2H, Ph); 7.38–7.36 (m, 3H, Ph); 7.26–7.17 (m, 5H, Ph); 4.50 (m, 2H, Cp subst.+CH$_2$); 4.40 (m, 1H, CH$_2$); 4.28 (m, 1H, Cp subst.); 4.07 (s, 5H, Cp); 3.72 (m, 1H, Cp subst.); 1.41 (t, 1H, OH).

$^{13}$C NMR (63 MHz, CDCl$_3$): δ139.4 (d, 1C, $J_{PC}$=9.7 Hz, Ph); 136.6 (d, 1C, $J_{PC}$=8.3 Hz, Ph); 134.5 (d, 2C, $J_{PC}$=20.8 Hz, Ph); 131.9 (d, 2C, $J_{PC}$=17.9 Hz, Ph); 128.9 (1C, Ph); 128.0 (d, 2C, $J_{PC}$=4.7 Hz, Ph); 127.8 (2C, Ph); 127.7 (1C, Ph); 92.3 (d, 1C, $J_{PC}$=23.4 Hz, Cp subst.); 75.3 (d, 1C, $J_{PC}$=7.4 Hz, Cp subst.); 71.2 (1C, Cp subst.); 71.1 (1C, Cp subst.); 69.3 (1C, Cp subst.); 69.1 (5C, Cp); 59.3 (d, 1C, $J_{PC}$=9.8 Hz, CH$_2$).

$^{31}$P NMR (101 MHz; CDCl$_3$): δ−22.80 (s, 1P)

MS (IE 70 eV):

m/z 402 (6%, M+2); 401 (32%, M+1); 400 (100%, M); 399 (50%, M−H); 262 (46%, M-FeCp-OH).

HRMS (IE 70 eV): Calculated 400.0679; Found 400.0679.

Elemental analysis

Calculated: C, 69.02%; H, 5.29%; P, 7.74%

Measured: C, 68.51%; H, 5.32%; P, 7.91%.

EXAMPLE 1B ($S_{Fc}$)-1-dicyclohexylphosphinomethyl-2-diphenylphosphinoferrocene Into a three-neck flask equipped with a reflux condenser, one places under argon 2 g of ($S_{Fc}$)-1-hydroxymethyl-2-diphenylphosphinoferrocene (M=400.26; 5 mmol) and then one injects 15 ml of degassed acetic anhydride. Heating to 80° C., the alcohol dissolves and acetylation is continued for 2 hours. The solution is then brought to ambient temperature and one adds 8 ml of toluene. By azeotropic distillation, the solvents are very rapidly evaporated under the vacuum of the still where the drying is continued for one night. This forms the acetate which is directly employed in the next step.

The acetate is a compound which can be isolated according to example 1C. The system is again placed under argon and one adds 30 ml of methanol and 10 g of dicyclohexylphosphine (M=198.29; 50.4 mmol). The reaction mixture is brought to reflux for one night, during which it turns black. After a return to ambient temperature and concentration under the vacuum of the still for 3 hours, an oil is formed.

This oil is purified by chromatography over alumina (200 g) under a slight pressure of argon (50 mbar). A first elution with hexane enables elimination of the excess of dicyclohexylphosphine which is directly destroyed at the column outlet over a large volume of Javel water solution. After elution of at least one liter, the hexane is replaced by toluene which enables distillation of a single product and isolation of 1.43 g of an orange oil. Recrystallization is performed by heating at reflux in 80 ml of degassed absolute ethanol and then cooling at −24° C. The yellow crystals formed are filtered and rinsed in ethanol. One obtains 1.30 g (2.24 mmol) of ($S_{Fc}$)-1-dicyclohexylphosphinomethyl-2-diphenylphosphinoferrocene with a yield of 45%.

mp=115° C.

$[\alpha]_D$=−160 (c=1.00; CHCl$_3$)

$^1$H NMR (250 MHz, CDCl$_3$): δ7.57–7.50 (m, 2H, Ph); 7.37–7.34 (m, 3H, Ph); 7.23–7.14 (m, 5H, Ph); 4.52 (s, 1H, Cp subst.); 4.19 (m, 1H, Cp subst.); 3.94 (s, 5H, Cp); 3.69 (s, 1H, Cp subst.); 2.68 (dd, 1H, $J_{AB}$=15.5 Hz and $J_{PH}$=2.3 Hz, CH$_2$); 2.58 (dd, 1H, $J_{AB}$=15.5 Hz and $J_{PH}$=2.2 Hz, CH$_2$); 1.76-1.00 (m, 22H, Cy).

$^{31}$P NMR (101 MHz; CDCl$_3$): δ−1.81 (d, 1P, $J_{PP}$=4.5 Hz, P-Cy); −23.41 (d, 1P, $J_{PP}$=4.5 Hz, P—Ph).

MS (IE 70 eV):

m/z 580 (4%, M); 497 (100%, M-Cy); 414 (6%, M-2Cy); 121 (7%, FeCp); 83 (11%, Cy); 56 (20%, Fe).

HRMS (IE 70 eV): Calculated 580.211; Found 580.211.

Elemental analysis:

Calculated: C, 72.41%; H, 7.30%; P, 10.67%.

Measured: C, 72.11%; H, 7.21%; P, 10.71%.

EXAMPLE 1C ($S_{Fc}$)-1-acetoxymethyl-2-diphenylphosphinoferrocene

In a Schlenk tube equipped with a reflux condenser under argon one reacts at 80° C. for 2 hours 800 mg of the compound of example 1A (2 mmol) with 8 ml of degassed acetic anhydride. After returning to ambient temperature, one adds 4 ml of toluene and the solution is concentrated under the vacuum of the still for one night so as to obtain an orange solid. This solid is dissolved in 5 ml of dichloromethane and filtered over a small height of silica which is rinsed with a hexane/ethyl acetate mixture (4:1). After evaporation of the solvents, one recrystallizes without heating the product obtained (710 mg) in 12 ml of hexane and 3 ml of dichloromethane by simple cooling at −18° C. The crystals formed are filtered and rinsed with hexane so as to obtain 290 mg of product. The mother liquors are concentrated for a second recrystallization (10 ml of hexane+2 ml of dichloromethane) which yields 260 mg. With a total of 550 mg (1.24 mmol), one obtains the recrystallized acetate with a yield of 62%.

mp=139° C.

$[\alpha]_D$=225 (c=1.00; CHCl$_3$)

$^1$H NMR (250 MHz, CDCl$_3$): δ7.54–7.35 (m, 5H, Ph); 7.24–7.14 (m, 5H, Ph); 5.14 (dd, 1H, $J_{AB}$=11.9 Hz and $J_{PH}$=2.3 Hz, CH$_2$); 4.94 (d, 1H, $J_{AB}$=11.9 Hz, CH$_2$); 4.51 (m, 1H, Cp subst.); 4.30 (m, 1H, Cp subst.); 4.05 (s, 5H, Cp); 3.75 (m, 1H, Cp subst,); 1.57 (s, 3H, CH$_3$).

$^{13}$C NMR (63 MHz, CDCl$_3$): δ170.2 (1C, CO); 139.4 (d, 1C, $J_{PC}$=10.2 Hz, Ph); 136.7 (d, 1C, $J_{PC}$=9.2 Hz, Ph); 134.7 (d, 2C, $J_{PC}$=20.8 Hz, Ph); 132.2 (d, 2C, $J_{PC}$=18.3 Hz, Ph); 128.9 (1C, Ph); 128.0 (d, 2C, $J_{PC}$=7.6 Hz, Ph); 127.7 (d, 2C, $J_{PC}$=6.4 Hz, Ph); 127.76 (1C, Ph); 86.0 (d, 1C, $J_{PC}$=24.1 Hz, Cp subst.); 77.3 (1C, Cp subst.); 72.8 (d, 1C, $J_{PC}$=3.4 Hz, Cp subst.); 72.0 (d, 1C, $J_{PC}$=3.8 Hz, Cp subst.); 69.8 (1C, Cp subst.); 69.4 (5C, Cp); 61.5 (d, 1C, $J_{PC}$=9.6 Hz, CH$_2$); 20.2 (1C, CH$_3$).

$^{31}$P NMR (101 MHz; CHCl$_3$): δ31 22.89 (s, 1P)

MS (IE 70 eV):

m/z 444 (8%, M+2); 443 (34%, M+1); 442 (91%, M); 377 (10%, M-Cp); 317 (24%, M-Cp-AcOH); 262 (73%, M-FeCp-AcO); 261 (46%, M-FeCp-AcOH); 121 (17%, FeCp); 59 (16%, AcO); 56 (22%, Fe); 43 (100%, Ac).

HR MS (IE 70 eV): Calculated 442.0785; Found 442.0785.

Elemental analysis

Calculated: C, 67.89%; H, 5.25%; P, 7.00%

Measured: C, 67.11%; H, 5.11%; P, 6.71%.

EXAMPLE 2

($S_{Fc}$)-1-diphenylphosphino-2-diphenylphosphinomethylferrocene

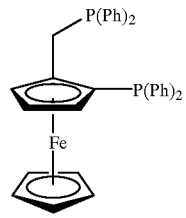

General procedure according to example 1 with:

1.20 g of the compound of example 1A (M=400.26; 3 mmol);

10 ml of degassed acetic anhydride;

5 ml of diphenylphosphine (M=186.20; d=1.07; 28.7 mmol);

30 ml of methanol.

After passage of the crude product over an alumina column, one obtains 0.63 g (1.11 mmol) of ($S_{Fc}$)-1-diphenylphosphino-2-diphenylphosphinomethylferrocene (yellow solid). The yield of the synthesis is 37%.

mp=92° C.

$[\alpha]_D$=−178 (c=1.00; CHCl$_3$)

$^1$H NMR (250 MHz, CDCl$_3$): δ7.62–7.50 (m, 2H, Ph); 7.43–7.19 (m, 18H, Ph); 4.13 (m, 1H, Cp subst.); 4.06 (s, 1H, Cp subst.); 3.96 (s, 5H, Cp); 3.75 (3, 1H, Cp subst.); 3.35 (s, 2H, CH$_2$).

$^{13}$C NMR (63 MHz, CDCl$_3$): δ139.9 (d, 1C, $J_{PC}$=9.1 Hz, Ph); 139.1 (d, 1C, $J_{PC}$=16.5 Hz, Ph); 138.8 (d, 1C, $J_{PC}$=16.2 Hz, Ph); 137.8 (d, 1C, $J_{PC}$=8.4 Hz, Ph); 135.0 (d, 2C, $J_{PC}$=21.3 Hz, Ph); 133.4 (d, 2C, $J_{PC}$=19.7 Hz, Ph); 132.3 (d, 2C, $J_{PC}$=17.4 Hz, Ph); 132.0 (d, 2C, $J_{PC}$=18 H Ph); 128.8 (d, 2C, $J_{PC}$=18.4 Hz, Ph); 128.3 (1C, Ph); 128.2 (2C, Ph); 128.1 (1C, Ph 128.0 (2C, Ph); 127.9 (2C, Ph); 127.7 (d, 2C, $J_{PC}$=15.4 Hz, Ph); 90.4 (dd, 1C, $J_{PC}$=26.9 and 16.7 Hz, Cp subst.); 75.6 (dd, 1C, $J_{PC}$=6.5 and 3.7 Hz, Cp subst.); 71.7 (dd, 1C, $J_{PC}$=7.3 and 3.8 Hz, Cp subst.); 70.5 (d, 1C, $J_{PC}$=3.6 Hz, Cp subst.); 69.8 (5C, Cp subst.); 68.9 (1C, Cp subst.); 28.8 (dd, 1C, $J_{PC}$=15.5 and 10.6 Hz, CH$_2$).

$^{31}$P NMR (101 MHz; CDCl$_3$): δ14.83 (d, 1P, $J_{PP}$=8 Hz, CH$_2$PPh$_2$); −23.35 (d, 1P, $J_{PP}$=8 Hz, FcPPh$_2$).

MS (IE 70 eV):

m/z 570 (9%, M+2); 569 (36%, M+1); 568 (71%, M); 491 (17%, M-Ph); 383 (100%, M-PPh$_2$); 306 (23%, M-PPh$_2$-Ph); 226 (12%, FeCpPPh); 121 (10%, FeCp).

HRMS (IE 70 eV): Calculated 568.1172; Found 568.1172.

Elemental analysis

Calculated: C, 73.95%; H, 5.32%; P, 10.90%; Fe, 9.83%

Measured: C, 74.18%; H, 5.22%; P, 10.87%; Fe, 9.65%.

EXAMPLE 3

($S_{Fc}$)-1-dicyclopentylphosphinomethyl-2-diphenylphosphinoferrocene

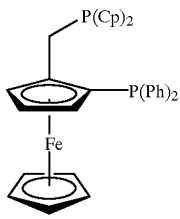

General procedure according to example 1 with:
1.60 g of the compound of example 1A (M=400.26; 3 mmol);
10 ml of degassed acetic anhydride;
5 g of dicyclopentylphosphine (M=170.23; 29.4 mmol);
20 ml of methanol.

After chromatography with toluene over alumina and an evaporation, one obtains 1.15 g (2.08 mmol) ($S_{Fc}$)-1-dicyclopentylphosphinomethyl-2-diphenylphosphinoferrocene (impure oil), corresponding to a yield of 52%.

$^1$H NMR (250 MHz, CDCl$_3$): δ7.62–7.53 (m, 2H, Ph); 7.38–7.36 (m, 3H, Ph); 7.25–7.21 (m, 5H, Ph); 4.58 (s, 1H, Cp subst.); 4.24 (m, 1H, Cp subst.); 3.95 (s, 5H, Cp); 3.77 (s, 1H, Cp subst.); 2.76 (s, 2H, CH$_2$); 1.82–1.3 (m, 18H, Cp).
$^{31}$P NMR (101 MHz, CDCl$_3$): δ3.10 (s, 1P, P–Cp); -23.81 (s, 1P, P-Ph).

General hydrogenation process:
The catalytic hydrogenation tests were performed in methanol or tetrahydrofuran, using rhodium complexes.

Preparation of the catalyst:
The cationic complexes for hydrogenation were prepared in situ by adding the calculated quantity of the compound of formula (I) to the rhodium complex [Rh(COD)$_2$]BF$_4$ formed from the complex [Rh(COD)$_2$(acac)] and ammonium hexafluorophosphate. The chlorinated rhodium complexes were also prepared in situ by adding the calculated quantity of the compound of formula (I) to the rhodium complex [Rh(Cl)(COD)]$_2$.

The catalysts can also be isolated as described in example 4.

EXAMPLE 4

[($S_{Fc}$)-1-dicyclopentylphosphinomethyl-2-diphenylphosphinoferrocene]cycloocta-1,5-dienerhodium hexafluorophosphate

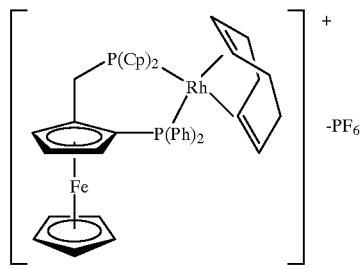

Into a Schlenk tube under argon, one places 190 mg of ($S_{Fc}$)-1-dicyclopentylphosphinomethyl-2-diphenylphosphinoferrocene (M=552.49; 0.34 mmol), 105 mg of [Rh(COD)(acac)] (M=301.23; 0.34 mmol) and 200 mg of NH$_4$PF$_6$ (M=163.00; 1.2 mmol). One covers this mixture with 5 ml of dichloromethane and 3 ml of water. After 2 hours of agitation, the aqueous phase is eliminated and the organic phase is washed twice with water; the solvent is then evaporated. On the crude solid, one adds 6 ml of benzene which is heated to reflux, with the complex remaining insoluble. After returning to ambient temperature and decantation, the supernatant is eliminated with a pipette. This operation is repeated twice, which results in 250 mg (0.27 mmol) of catalyst with a yield of 80%.

mp=178° C. [α]$_D$=+15 (c=0.39; CHCl$_3$)

$^1$H NMR (250 MHz, CDCl$_3$): δ8.43–8.27 (m, 2H, Ph); 7.75–7.69 (m, 3H, Ph); 7.43–7.24 (m, 5H, Ph); 5.25 (s, 1H, COD); 5.09 (s, 1H, COD); 4.71 (s, 1H, Cp subst.); 4.36 (s, 1H, COD); 4.32 (s, 1H, Cp subst.); 4.25 (s, 1H, Cp subst.); 3.65 (s, 5H, Cp); 3.41 (s, 1H, COD); 3.07 (m, 1H, COD); 2.50–1.23 (m, 27H, CH$_2$+2xCp+COD).

$^{31}$P NMR (101 MHz; CDCl$_3$): δ46.09 (dd, 1P, J$_{PP}$=32.8 Hz and J$_{PRh}$=144 Hz, P-Cp); 19.16 (dd, 1P, J$_{PP}$=32.8 Hz and J$_{PRh}$=144.6 Hz, P—Ph); -143.78 (m, 1P, J$_{PP}$=711 Hz, PF$_6$).

EXAMPLE 5

Bis(cycloocta-1,5-diene)rhodium tetrafluoroborate

Into a Schlenk tube under argon, one places 212 mg of chlorocycloocta-1,5-dienerhodium dimer (M=493.08; 0.43 mmol) and 177 mg of silver tetrafluoroborate (M=194.68; 0.91 mmol) in solution in 15 ml of dichloromethane; one then adds 111 µl of cycloocta-1,5-diene (M=108.18; d =0.882; 0.91 mmol) and agitation is implemented for 2 hours. An abundant precipitate of silver chloride appears. One decants the medium and transfers, via a filtration tube, the maroon supernatant solution into another Schlenk tube before eliminating the solvent. The crude product is washed with 5 ml of THF and then dried on the still to obtain 290 mg (0.71 mmol) of the complex with a yield of 83%.

mp: 204° C.

1H NMR (250 MHz, CDCl$_3$): δ5.32 (s, 8H, 8xCH); 2.68–2.35 (m, 16H, 8xCH$_2$).

Hydrogenation process:

The substrate is introduced into an autoclave that one connects to a glass filter pump and a bottle of hydrogen which enables purging of the system. Under a hydrogen atmosphere, one adds via a syringe the catalytic solution prepared under argon in a Schlenk tube by mixing for 10 minutes 1% of [Rh(COD)$_2$]BF$_4$ and 1.3% of ligand in 10 ml of methanol. The reactor is then filled at the desired pressure and intense agitation is continued for 12 hours. After the reaction, the methanol is evaporated.

In the table below, we present the results obtained with the unsaturated enamides, acids and esters.

The enantiomeric excesses (e.e.) were measured by HPLC on the chiral phase.

Rh: [Rh(cyclooctadiene)$_2$Cl]$_2$

RH+: [Rh(cyclooctadiene)$_2$]BF$_4$

Substrate/catalyst: 100

Hydrogen pressure: 1 atmosphere
Substrate 1: (Z)-alpha-acetamidocinnamic acid.

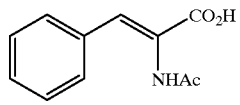

Substrate 2: methyl (Z)-alpha-acetamidocinnamate
Substrate 3: (E)-N-(1-phenyl-1-propenyl)-acetamide

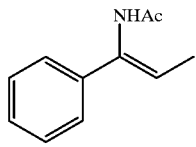

Substrate 4: itaconic acid

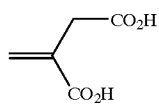

Substrate 5: dimethyl itaconate
Substrate 6: atropic acid

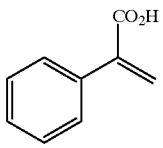

Temperature: 25° C.
Ligand/Rh=1.3
Substrate/catalyst=100

| Sub-strate | Catalytic complex/ligand | $H_2$ P. | Solvent | Reaction time | Yield (%) | e.e. (%)/ Conf. |
|---|---|---|---|---|---|---|
| S1 | $Rh^0$/(S) ex. 2 | 5 atm | $CH_3OH$ | >10 h | 86 | 77 (S) |
| S2 | $Rh^+$/(S) ex. 2 | 1 atm | $CH_3OH$ | 1 h | 97 | 65 (S) |
| S3 | $Rh^+$/(S) ex. 1 | 1 atm | $CH_3OH$ | 2 h 50 min | 99 | 94 (R) |
| S4 | $Rh^+$/(S) ex. 1 | 1 atm | $CH_3OH$ | 2 h 40 min | 92 | 93 (S) |
|  | $Rh^+$/(S) ex. 3 | // | // | // | 98 | 88 (S) |
| S5 | $Rh^+$/(S) ex. 1 | 1 atm | THF | 2 h 45 min | 94 | 97 (S) |
|  | $Rh^+$/(S) ex. 1 | 1 atm |  | 45 min | 94 | 98 (S) |
|  | Example 4 | 1 atm | / | <10 min | 95 | 92 (S) |
| S6 | $Rh^+$/(S) ex. 1 | 5 atm | $CH_3OH$ | / | 87 | 81 (R) |

What is claimed is:

1. An enantioselective reduction process comprising reducing unsaturated substrate compounds of formula (IV)

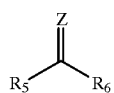

(IV)

in which R5 and R6 are different, with R5 selected from among a $C_{1-5}$ alkyl; an aryl group; an aryl group substituted by a $C_{1-4}$ alkyl, a $C_{1-4}$ alkoxy or a halogen; a carboxylic acid; a carboxylic ester; a $C_{1-4}$ alkyl carboxylic acid; a $C_{1-4}$ alkyl carboxylate; with R6 selected from among an amide; an aryl; an aryl substituted by a $C_{1-4}$ alkyl, a $C_{1-4}$ alkoxy or a halogen heteroaryl; a heteroaryl substituted by a $C_{1-4}$ alkyl, a $C_{1-4}$ alkoxy or a halogen; in which Z is represented by an NR7, NOR7 or $C(R7)_2$ group, with R7 selected from among hydrogen; a $C_{1-5}$ alkyl; an aryl group optionally substituted by a $C_{1-4}$ alkyl; a halogen or an alkoxyalkyl; a heteroaryl group optionally substituted by a $C_{1-4}$ alkyl or halogen or an alkoxyalkyl in the presence of a transition metal complex and a ferrocene phosphine according to formula (I)

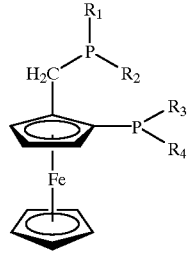

(I)

in which R1, R2, R3, and R4 are identical or different and represent a group selected from among hydrogen, a linear or branched $C_{1-7}$ alkyl, a $C_{5-7}$ cycloalkyl optionally substituted by a $C_{1-4}$ alkyl, a trifluoromethyl, a halogen, a hydroxy or an alkoxy, a phenyl optionally substituted by a $C_{1-4}$ alkyl, a trifluoromethyl, a halogen, a hydroxy or an alkoxy.

2. An enantioselective reduction process unsaturated compounds bearing functional groups of formula (IV) as defined in claim 1, comprising:

a) mixing a ferrocene phosphine of formula (I), (I)

in which R1, R2, R3, and R4 are identical or different and represent a group selected from among hydrogen, a linear or branched $C_{1-7}$ alkyl, a $C_{5-7}$ cycloalkyl optionally substituted by a $C_{1-4}$ alkyl, a trifluoromethyl, a halogen, a hydroxy or an alkoxy, a phenyl optionally substituted by a $C_{1-4}$ alkyl, a trifluoromethyl, a halogen, a hydroxy or an alkoxy, with an unsaturated substrate compound of formula (IV)

(IV)

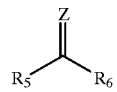

in which R5 and R6 are different, with R5 selected from among a $C_{1-5}$ alkyl, an aryl group; an aryl group substituted by a $C_{1-4}$ alkyl, a $C_{1-4}$ alkoxy or a halogen; a carboxylic acid; a carboxylic ester; a $C_{1-4}$ alkyl carboxylic acid; a $C_{1-4}$ alkyl carboxylate; with R6 selected from among an amide; an aryl; an aryl substituted by a $C_{1-4}$ alkyl, a $C_{1-4}$ alkoxy or a halogen heteroaryl; a heteroaryl substituted by a $C_{1-4}$ alkyl, a $C_{1-4}$ alkoxy or a halogen; in which Z is represented by an NR7, NOR7 or $C(R7)_2$ group, with R7 selected from among hydrogen; a $C_{1-5}$ alkyl; an aryl group optionally substituted by a $C_{1-4}$ alkyl; a halogen or an alkoxyalkyl; a heteroaryl group optionally substituted by a $C_{1-4}$ alkyl or halogen or an alkoxyalkyl; under a hydrogen atmosphere, and in the presence of a transition metal complex;

b) bringing the mixture to a temperature between 20 and 100° C. to form optically active, hydrogenated compound of formula (IV)

c) recovering the optically active, hydrogenated compound of formula (IV) from the mixture.

3. The process according to claim 2, wherein the transition metal of said complex is rhodium and wherein said complex is selected from Rh(COD)(acac), (Rh(COD))BF$_4$, and (Rh(Cl)(COD)$_2$.

4. The process according to claim 2 or 3 wherein the quantity of formula (IV) substrate in relation to the quantity of the transition metal complex is from 1 to 50,000.

5. The process according to claims 2 or 3, wherein the quantity of formula (IV) substrate in relation to the quantity of the transition metal complex is from 100 to 20,000.

6. The process according to claims 2 or 3, wherein the quantity of formula (IV) substrate in relation to the quantity of the transition metal complex is from 1000 to 10,000.

7. An enantioselective process comprising the steps of: introducing a ferrocene phosphine of formula (I):

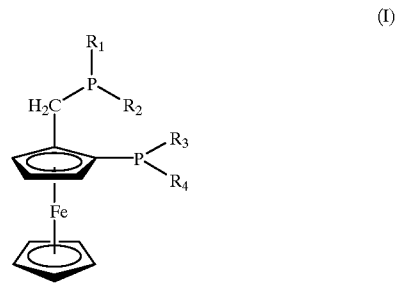

in which R1, R2, R3, and R4 are identical or different and represent a group selected from among hydrogen, a linear or branched $C_{1-7}$ alkyl, a $C_{5-7}$ cycloalkyl optionally substituted by a $C_{1-4}$ alkyl, a trifluoromethyl, a halogen, a hydroxy or an alkoxy, a phenyl optionally substituted by a $C_{1-4}$ alkyl, a trifluoromethyl, a halogen, a hydroxy or an alkoxy;

introducing a substrate compound of formula (IV):

(IV)

in which R5 and R6 are different, with R5 selected from among a $C_{1-5}$ alkyl; an aryl group; an aryl group substituted by a $C_{1-4}$ alkyl, a $C_{1-4}$ alkoxy or a halogen; a carboxylic acid; a carboxylic ester; a $C_{1-4}$ alkyl carboxylic acid; a $C_{1-4}$ alkyl carboxylate; with R6 selected from among an amide; an aryl; an aryl substituted by a $C_{1-4}$ alkyl, a $C_{1-4}$ alkoxy or a halogen heteroaryl; a heteroaryl substituted by a $C_{1-4}$ alkyl, a $C_{1-4}$ alkoxy or a halogen; in which Z is represented by an NR7, NOR7 or $C(R7)_2$ group, with R7 selected from among hydrogen; a $C_{1-5}$ alkyl; an aryl group optionally substituted by a $C_{1-4}$ alkyl; a halogen or an alkoxyalkyl; a heteroaryl group optionally substituted by a $C_{1-4}$ alkyl or halogen or an alkoxyalkyl;

mixing said ferrocene phosphine and said substrate, under a hydrogen atmosphere, in the presence of a transition metal complex selected from (Rh(COD)(acac)), (Rh(COD))BF$_4$, and (Rh(Cl)COD)$_2$;

bringing said mixture to a temperature of 20 to 100° C.; and recovering optically active, hydrogenated product.

* * * * *